United States Patent [19]

Kroenke

[11] 4,410,463
[45] Oct. 18, 1983

[54] TETRAPENTYLAMMONIUM MOLYBDATES

[75] Inventor: William J. Kroenke, Brecksville, Ohio

[73] Assignee: The B. F. Goodrich Company, Akron, Ohio

[21] Appl. No.: 402,481

[22] Filed: Jul. 28, 1982

[51] Int. Cl.³ ............................................. C07F 11/00
[52] U.S. Cl. ........................ 260/429 R; 260/45.75 R
[58] Field of Search ................................... 260/429 R

[56] References Cited

U.S. PATENT DOCUMENTS

| | | | |
|---|---|---|---|
| 3,223,625 | 12/1965 | Cyphers et al. | 260/429 R X |
| 3,290,245 | 12/1966 | Elliott et al. | 260/429 R X |
| 3,349,108 | 10/1967 | Marzluff | 260/429 R |
| 4,053,455 | 10/1977 | Kroenke | 260/429 R X |
| 4,153,792 | 5/1979 | Kroenke | 260/429 R X |
| 4,217,292 | 8/1980 | Kroenke | 260/429 R |
| 4,234,474 | 11/1980 | Kroenke | 260/429 R X |
| 4,235,770 | 11/1980 | Kroenke | 260/429 R X |
| 4,247,451 | 1/1981 | Kroenke | 260/429 R X |
| 4,248,766 | 2/1981 | Kroenke | 260/429 R X |
| 4,248,767 | 2/1981 | Kroenke | 260/429 R X |

*Primary Examiner*—Helen M. S. Sneed
*Attorney, Agent, or Firm*—James R. Lindsay

[57] ABSTRACT

Tetrapentylammonium molybdates having the empirical formula $$[(C_5H_{11})_4N]_a Mo_b O_c H_d$$

where a, b and c are (2,2,7); (3,5,17); (2,6,19); (6,7,24) or (4,8,26) and d is 0 or 1 are disclosed as novel amine molybdates which are useful as smoke retardant additives for vinyl chloride polymer compositions.

6 Claims, No Drawings

TETRAPENTYLAMMONIUM MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 4 hours.

Amine molybdates also may be produced, as described in U.S. Pat. No. 4,217,292, by reacting essentially stoichiometric quantities of molybdenum trioxide with an amine or an amine salt in an aqueous medium essentially free of acid and in which a water-soluble ammonium or monovalent metal or divalent metal or trivalent rare earth metal salt of an inorganic or organic acid is dissolved. Sometimes the reaction is carried out in a polar organic solvent instead of water.

The particular amine molybdate formed may depend upon which process is used to form the amine molybdates and the quantity of reactants present in the reaction mixture, as well as the reaction condition.

SUMMARY OF THE INVENTION

The present invention pertains to a class of novel molybdates, namely, tetrapentylammonium molybdates, which may be represented by the formula $$[(C_5H_{11})_4N]_a Mo_b O_c H_d$$

where a,b and c are (2,2,7); (3,5,17); 2,6,19); 6,7,24) or (4,8,26) and d is 0 or 1. Like many other amine molybdates, the tetrapentylammonium molybdates function as effective smoke retardant additives for vinyl chloride polymer.

DETAILED DESCRIPTION OF THE INVENTION

Tetrapentylammonium molybdates may be produced by reacting ammonium dimolybdate [$(NH_4)_2Mo_2O_7$] and tetrapentylammonium bromide [$(C_5H_{11})_4N$]Br in an acidic aqueous medium. Suitable acids include inorganic acids, such as hydrochloric acid, nitric acid, or sulfuric acid, or mixtures thereof, or organic acids, such as acetic acid, propionic acid, or benzoic acid. The amount of acid used may be varied widely from about ½ to 10 or more molar equivalents of acid per molar equivalent of ammonium dimolybdate. However, about 1/1 molar equivalent ratio is preferred. Sufficient water is included in the reaction mixture to insure a reaction mixture that has a consistency that enables it to be easily stirred. The mixture is heated to reflux and refluxed for about 10 minutes to 16 hours, preferably while being stirred continuously. After the reaction is completed, the solid reaction product is separated from the aqueous medium by filtration, centrifugation, or other suitable separation procedure. The recovered solid reaction product desirably is washed with water and then is dried. The molar ratio of ammonium dimolybdate to tetrapentylammonium bromide will influence which tetrapentylammonium molybdate product is formed as a result of the reaction. Theoretical molybdate/tetrapentylammonium bromide molar ratios from 0.5/1 to 3/1 are used. However, the actual molar ratios that can be used in the reaction can be outside the stated range.

Not all of the realizable tetrapentylammonium molybdates can be conveniently prepared directly by the process described. Some can be best prepared by reacting previously formed tetrapentylammonium molybdates with either a strong inorganic acid, such as hydrochloric acid, or tetrapentylammonium hydroxide in polar solvents, such as water, methanol and acetonitrile.

The tetrapentylammonium molybdates within the scope of the present invention are tetrapentylammonium dimolybdate [$(C_5H_{11})_4N]_2Mo_2O_7$, tetrapentylammonium hexamolybdate [$(C_5H_{11})_4N]_2Mo_6O_{19}$, tetrapentylammonium pentamolybdate [$(C_5H_{11})_4N]_3Mo_5O_{17}H$, tetrapentylammonium heptamolybdate [$(C_5H_{11})_4N]_6Mo_7O_{24}$ and tetrapentylammonium octamolybdate [$(C_5H_{11})_4N]_4Mo_8O_{26}$.

The following examples mre fully illustrate the preparation of the novel tetrapentylammonium molybdates of the present invention.

EXAMPLE I 2.60 grams of 37 percent hydrochloric acid solution were mixed with 200 milliliters of water and, together with 10.00 grams of tetrapentylammonium bromide, were added to a 500 milliliter round-bottom flask equipped with a water-cooled condenser and a mechanical stirrer. 8.98 grams of ammonium dimolybdate were dissolved in 50 milliliters of hot water and were added to the flask. The mixture in the flask was heated to refulx and refluxed for 30 minutes. The contents of the flask were filtered through a Buchner funnel, a yellow residue being retained on the filter paper. The residue was washed three times with about 50 milliliters of water and dried in a vacuum oven maintained at about 75° C. for 3 hours. 13.77 grams of residue were recovered which was identified by infrared analysis to be a mixture of tetrapentylammonium hexamolybdate and tetrapentylammonium alpha-octamolybdate.

EXAMPLE II 9.51 grams of tetrapentylammonium alpha-octamolybdate ([$(C_5H_{11})_4N]_4Mo_8O_{26}$) and 80 milliliters of acetonitrile were charged into a 125 milliliter Erlenmeyer flask and stirred. 4.95 grams of tetrabutylammonium hydroxide dissolved in 50 milliliters of ethanol were added to the flask. The contents of the flask were stirred until dissolution was substantially complete. The solution was filtered to remove any undissolved component and combined with ether. An oily layer formed. The oily layer was separated from the ether and dissolved in acetonitrile. Ether was added to the solution with stirring until an oily layer again was formed. The solvent layer was decanted from the oily layer. The oily layer again was dissolved in acetonitrile. The solution was rotoevaporated to dryness. A cream colored viscous liquid, identified by infrared analysis to be tetrapentylammonium dimolybdate, was recovered.

EXAMPLE III 2.25 grams of tetrapentylammonium dimolybdate was added to a 100 milliliter Erlenmeyer flask. 0.20 gram of a 37 percent hydrochloric acid solution was mixed with 50 milliliters of water and added to the flask. The contents of the flask were stirred for 5 minutes. A solid precipitate was formed. The contents of the flask were filtered. A cream-yellow solid residue was recovered and dried in a vacuum oven at 25° C. for 16 hours. Infrared analysis identified the residue as tetrapentylammonium pentamolybdate.

EXAMPLE IV 4.76 grams of tetrapentylammonium alpha-octamolybdate and 20 milliliters of acetonitrile were added to a 50 milliliter Erlenmeyer flask and stirred. 0.05 milliliter of a 37 percent hydrochloric acid solution was added to the flask. The contents of the flask were stirred at room temperature (about 25° C.) for ½ hour. A yellow precipitate formed. The contents of the flask were filtered. The yellow solid residue was dried in a vacuum oven at 25° C. for 16 hours. Infrared analysis identified the residue as tetrapentylammonium hexamolybdate.

EXAMPLE V 21.19 grams of tetrapentylammonium bromide and 1000 milliliters of water were added to a 2000 milliliter beaker and stirred together until the tetrapentylammonium bromide dissolved in the water. 19.77 grams of ammonium heptamolybdate was dissolved in 200 milliliters of water and added to the beaker. The contents of the beaker were stirred for 2 minutes. A white precipitate formed. The contents of the beaker were filtered. The precipitate was dried in a vacuum oven for two days at room temperature. Infrared analysis identified the white crystalline solid as tetrapentylammonium alpha-octamolybdate.

EXAMPLE VI 2.0 grams of ammonium heptamolybdate and 20 milliliters of water were added to a 50 milliliter Erlenmeyer flask equipped with a mechanical stirrer and stirred together until the ammonium heptamolybdate had dissolved in the water. 2.12 grams of tetrapentylammonium bromide were added to the flask. The contents of the flask were stirred for 15 minutes. An off-white precipitate was formed. The contents of the flask were filtered. The residue was washed with separate washes of water, ethanol, acetone and ether. The washed residue was dried in a vacuum oven at 25° C. for two hours. Infrared analysis identified the residue as being impure tetrapentylammonium beta-octamolybdate. The residue then was dissolved in 20 milliliters of acetonitrile and stored at approximately −10° C. for 16 hours. The solution was filtered and the residue was vacuum dried at 25° C. for two hours. The off-white crystalline residue was identified by infrared analysis to be tetrapentylammonium beta-octamolybdate.

The tetrapentylammonium molybdates have been found to be smoke retardant additives for vinyl chloride polymer compositions. When used as a smoke retardant additive, the tetrapentylammonium molybdates desirably either are combined with the other ingredients of the vinyl chloride polymer composition on a roll mill or added by any other convenient mixing procedure. Preferably, from about 0.1 to about 20 parts by weight of a tetrapentylammonium molybdate is used per 100 parts by weight of vinyl chloride polymer.

Vinyl chloride polymers with which the tetrapentylammonium molybdates can be used as smoke retardant additives include homopolymers, copolymers and blends of homopolymers and/or copolymers, and include chlorinated polymers thereof. The vinyl chloride polymers may contain from 0 to 50 percent by weight of at least one other olefinically unsaturated monomer. Suitable monomers include 1-olefins containing from 2 to 12 carbon atoms such as ethylene, propylene, 1-butene, isobutylene, 1-hexene, 4-methyl-1-pentene, and the like; dienes containing from 4 to 10 carbon atoms, including conjugated dienes such as butadiene, isoprene, piperylene, and the like; ethylidene norbornene and dicyclopentadiene; vinyl esters and allyl esters such as vinyl acetate, vinyl chloroacetate, vinyl propionate, vinyl laurate, alkyl acetate, and the like; vinyl aromatics such as styrene, α-methyl styrene, chlorostyrene, vinyl toluene, vinyl naphthalene, and the like; vinyl allyl ethers and ketones such as vinyl methyl ether, allyl methyl ether, vinyl isobutyl ether, vinyl n-butyl ether, vinyl chloroethyl ether, methylvinyl ketone, and the like; vinyl nitriles such as acrylonitrile, methacrylonitrile, and the like; cyanoalkyl acrylates such as α-cyanomethyl acrylate, the α-β- and α-cyanopropyl acrylate, and the like; olefinically unsaturated acids and esters thereof including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecylacrylate, methoxyethyl acrylate, ethoxyethyl acrylate, hexylthioethyl acrylate, methyl methacrylate, ethyl methacrylate, butyl methacrylate, and the like.

The vinyl chloride polymer, in addition to the tetrapentylammonium molybdate, may contain the usual compounding ingredients known to the art such as fillers, stabilizers, opacifiers, lubricants, processing aids, impact modifiers, plasticizers, antioxidants, and the like.

Smoke retardancy may be measured using an NBS Smoke Chamber according to procedures described in ASTM E662-79 "Test For Specific Optical Density Of Smoke Generated By Solid Materials". Maximum smoke density (Dm) is a dimensionless number and has the advantage of representing a smoke density independent of chamber volume, specimen size or photometer path length, provided a consistent dimensional system is used. Percent smoke reduction is calculated using the equation:

$$\frac{Dm/g \text{ of control} - Dm/g \text{ of sample}}{Dm/g \text{ of control}} \times 100.$$

The term "Dm/g" means maximum smoke density per gram of material. Dm and other aspects of the physical optics of light transmission through smoke are discussed fully in the ASTM publication.

Smoke retardance also may be measured using the Goodrich Smoke-Char Test. Test samples may be prepared by dry blending polymer resin and smoke retardant additives. The blend is ground in a liquid $N_2$-cooled grinder to assure uniform dispersion of the somke retardant additives in the resin. Small (about 0.3 g) samples of the polymer blend are pressed into pellets about ¼ inch diameter for testing. Alternatively, test samples may be prepared by blending resin, smoke retardant additives and lubricant(s) or processing aid(s) in a blender such as an Osterizer blender. The blend is milled, pressed into sheets, and cut into small (about 0.3 gram) samples for testing. The test samples are placed on a screen and burned for 60 seconds with a propane gas flame rising vertically from beneath the samples. Sample geometry at a constant weight has been found not to be significant for the small samples used in this test. A Bernz-O-Matic pencil flame burner head is used with gas pressure maintained at about 40 psig. Each sample is immersed totally and continuously in the flame. Smoke from the burning sample rises in a vertical chimney and passes through the light beam of a Model 407 Precision Wideband Photometer (Grace Electronics, Inc., Cleveland, Ohio) coupled with a photometer integrator. Smoke generation is measured as integrated area per gram of sample.

The smoke retardant property of tetrapentylammonium molybdates is illustrated by the following example:

EXAMPLE VII

The following recipe was used:

| Material | Parts by Weight |
|---|---|
| Polyvinyl Chloride resin* | 100.0 |
| Lubricant** | 2.0 |
| Tin Stabilizer*** | 2.0 |
| Tetrapentylammonium molybdate | Varied |

*Homopolymer of vinyl chloride having an inherent viscosity of about 0.98–1.04; ASTM classification GO-5-15543.
**A commercial polyethylene powder lubricant (Microthene 510).
***Tin Thioglycolate 2.0 grams of the mixture of tetrapentylammonium hexamolybdate and tetrapentylammonium alpha-molybdate of Example I were mixed with 100.0 grams of the polyvinyl chloride resin of the aforesaid recipe on a two-roll mill. The lubricant and tin stabilizer of the recipe were added to the molybdate-polyvinyl chloride resin mixture and the resulting composition was milled on the mill for about 5 minutes at a roll temperature of about 165° C. The milled composition was pressed into a 6×6×0.050 inch sheet. Pressing was done at about 160° C. for 5 minutes using 40,000 pounds (about 14,900 Kg) of force applied to a 4-inch ram. The sample (Sample 1) received a 2 minute preheat before being pressed.

A sample (Sample 2) was prepared as described above except that 5.0 grams of the tetrapentylammonium molybdate mixture of Example I were used in the recipe instead of 2.0 grams of the mixture of Example I.

The molded samples were cut into 2−7/8×2−7/8×0.50 inch sections and tested against a control sample formed utilizing the aforesaid recipe but without use of the molybdate additive. Testing was performed using the flaming mode of the NBS Smoke Chamber Test (ASTM E662-79) described hereinabove. The test results are given in Table I.

TABLE I

| Sample | Dm/g* | Smoke Reduction (%) |
|---|---|---|
| Control | 60.8 | — |
| 1 | 34.6 | 43.1 |
| 2 | 30.5 | 49.9 |

*Dm/g = maximum smoke density per gram of sample.

0.075 gram of the tetrapentylammonium dimolybdate of Example II was blended in a liquid nitrogen-cooled grinder with 1.50 grams of polyvinyl chloride resin (homopolymer of vinyl chloride having an inherent viscosity of about 0.98–1.04, ASTM classification GO-5-15543) as described above. The mixture (Sample 3) was cold pressed into ¼ inch diameter pellets weighing about 0.3 gram each.

0.075 gram of the tetrapentylammonium pentamolybdate of Example III was blended with 1.50 grams of polyvinyl chloride resin (same type as described above) in a liquid nitrogen-cooled grinder. The blend (Sample 4) was formed into pellets as described above.

Similar pellets were formed from a mixture (Sample 5) of 0.075 gram of the tetrapentylammonium hexamolybdate of Example IV and 1.50 grams of polyvinyl chloride resin (same type as described above), from a mixture (Sample 6) of 0.075 gram of the tetrapentylammonium alpha-octamolybdate of Example V and 1.50 grams of polyvinyl chloride resin (same type as described above), and from a mixture (Sample 7) of 0.075 gram of the tetrapentylammonium beta-octamolybdate of Example VI and 1.50 grams of polyvinyl chloride resin (same type as described above). Pellets formed from the polyvinyl chloride resin (without additive) were prepared as a "control".

Testing for smoke reduction was performed using the Goodrich Smoke-Char Test described above. The test results are set forth in Table II.

TABLE II

| Sample | Spvc* | Smoke Reduction (%) |
|---|---|---|
| Control | 65.0 | — |
| 3 | 50.6 | 22.2 |
| 4 | 40.2 | 38.2 |
| 5 | 35.9 | 44.8 |
| 6 | 39.6 | 39.1 |
| 7 | 37.2 | 42.8 |

*Smoke-char smoke number per gram of polyvinyl chloride resin in sample blend.

The improved smoke retardant vinyl chloride polymer compositions obtained by the inclusion of a tetrapentylammonium molybdate in the composition are useful wherever smoke reduction is a desirable property, such as in carpeting, house siding, plastic components for aircraft and passenger car interiors, and the like.

I claim:

1. Tetrapentylammonium molybdates having the empirical formula

$$[(C_5H_{11})_4N]_a Mo_b O_c H_d$$

where a, b and c are (2,2,7); (3,5,17); (2,6,19); (6,7,24) or (4,8,26) and d is 0 or 1.

2. The tetrapentylammonium molybdate of claim 1 wherein a is 2, b is 2, c is 7 and d is 0.

3. The tetrapentylammonium molybdate of claim 1 wherein a is 3, b is 5, c is 17, and d is 1.

4. The tetrapentylammonium molybdate of claim 1 wherein a is 2, b is 6, c is 19, and d is 0.

5. The tetrapentylammonium molybdate of claim 1 wherein a is 6, b is 7, c is 24, and d is 0.

6. The tetrapentylammonium molybdate of claim 1 wherein a is 4, b is 8, c is 26, and d is 0.

* * * * *